United States Patent
Yamada et al.

(10) Patent No.: US 7,038,091 B2
(45) Date of Patent: May 2, 2006

(54) PROCESS FOR PRODUCING ACETYLENE COMPOUND

(75) Inventors: Osamu Yamada, Funabashi (JP); Hiroo Matsumoto, Funabashi (JP); Takanori Shimizu, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/531,458

(22) PCT Filed: Sep. 26, 2003

(86) PCT No.: PCT/JP03/12312

§ 371 (c)(1),
(2), (4) Date: Apr. 14, 2005

(87) PCT Pub. No.: WO2004/035520

PCT Pub. Date: Apr. 29, 2004

(65) Prior Publication Data

US 2006/0041031 A1 Feb. 23, 2006

(30) Foreign Application Priority Data

Oct. 18, 2002 (JP) .............................. 2002-303876

(51) Int. Cl.
*C07C 205/00* (2006.01)
(52) U.S. Cl. ..................................... 568/583
(58) Field of Classification Search .................. 568/583
See application file for complete search history.

(56) References Cited

U.S. PATENT DOCUMENTS 4,542,149 A    9/1985   Evans et al.

FOREIGN PATENT DOCUMENTS

JP       A 58-188880     11/1983

OTHER PUBLICATIONS

Evans et al; "Synthesis and Antihypertensive Activity of Substituted trans-4-Amino-3, 4-dihydro-2,2-dimethyl-2H-1-benzopyran-3-ols"; J. Med. Chem. 1983, pp. 1582-1589.
Bell et al; "Copper(I) Iodide: A Catalyst for the Improved Synthesis of Aryl Propargyl Ethers"; SYNTHESIS; Jun. 1995 pp. 707-712.
Godfrey et al; "Improved Synthesis of Aryl 1,1-Dimethylpropargyl Ethers"; Tetrahedron Letters, vol. 35, No. 35, 1994, pp. 6405-6408.
Subramanian et al; "A Facile Synthesis of Aryl Ethers of Ethynylcarbinols Using the Mitsunobu Reaction"; Synthetic Communications, 1989, pp. 1255-1259.
Harfenist et al; "The Influence of Structure on the Rate of Thermal Rearrangement of Aryl Propargyl Ethers to the Chromenes. The gem-Dimethyl Effect"; J. Org. Chem., vol. 37, No. 6, 1972, pp. 841-848.
Raeppel et al; "Novel Exploration of the $S_NAr$ Reaction"; SYNLETT; Apr. 14, 1998, pp. 794-796.
Xu et al; "Polymer Supported Bases in Combinatorial Chemistry: Synthesis of Aryl Ethers from Phenols and Alkyl Halides and Aryl Halides"; Tetrahedron Letters, vol. 38, No. 42, 1997, pp. 7337-7340.

*Primary Examiner*—J. Parsa
(74) *Attorney, Agent, or Firm*—Oliff & Berridge, PLC

(57) ABSTRACT

There is provided a process for producing an acetylene compound useful as an intermediate of pharmaceuticals, from 4-nitrofluorobenzene, in industrially and economically advantageous manner.

Concretely, it is a method for producing an acetylene compound of formula (3)

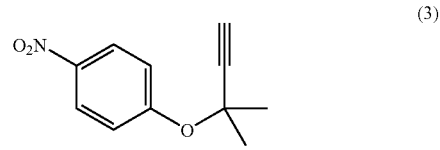

(3)

characterized by reacting 4-nitrofluorobenzene of formula (1)

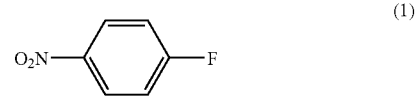

(1)

with an alkoxide of 2-methyl-3-butyn-2-ol of formula (2)

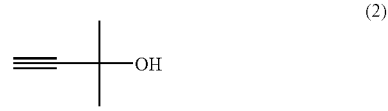

(2)

at −20 to 10° C.

4 Claims, No Drawings

PROCESS FOR PRODUCING ACETYLENE COMPOUND

TECHNICAL FIELD

The present invention relates to a process for producing an acetylene compound from 4-nitrofluorobenzene and 2-methyl-3-butyn-2-ol. This compound is useful as an intermediate for synthesizing e.g., antifibrillatory agents (see, JP-A2001-151767) or hypotensive agents (see, *J. Med. Chem.*, 1983, Vol. 26, No. 11, 1582–1589).

BACKGROUND ART

As the prior method for producing an acetylene compound of formula (3), there is known a method in which 4-nitrophenol (compound (5)) is reacted with 2-methyl-3-butyn-2-chloride (compound (6)) in the presence of a base (see, for example *J. Med. Chem.*, 1983, vol. 26, No. 11, p. 1582 and JP-A-58-188880).

It is also reported a method in which 4-nitrophenol (compound (5)) is reacted with 2-methyl-3-butyn-2-chloride (compound (6), in the presence of copper iodide catalyst, potassium iodide and potassium carbonate (see, for example *Synthesis*, 1995, vol. 6, p. 707).

Also, it is reported a method in which 4-nitrophenol (compound (5)) is reacted with a derivative of 2-methyl-3-butyn-2-ol (compound (7)) in the presence of copper catalyst and DBU (1,8-diazabicyclo[5.4.0]undec-7-ene) (see, for example *Tetrahedron Lett.*, 1994, vol. 35, p. 6405).

In addition, it is reported a method in which 4-nitrophenol (compound (5)) is reacted with 2-methyl-3-butyn-2-ol in the presence of triphenylphosphine and DEAD (diethyl azodicarboxylate) (Mitsunobu Reaction, see, for example *Synth. Commun.*, 1989, vol. 19, p. 1255).

As the preparing method by using 4-nitrofluorobenzene as a raw material, there is known a method in which 2-methyl-3-butyn-2-ol is used instead of a solvent, and the raw material is reacted with potassium alkoxide of 2-methyl-3-butyn-2-ol (see, for example *J. Org. Chem.*, 1972, vol. 37, p. 841).

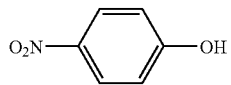

(5)

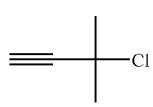

(6)

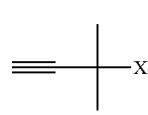

(7)

(wherein X means Cl, —OCO$_2$CH$_3$ or —OCOCF$_3$.)

The preparing method described in *J. Med. Chem.*, 1983, vol. 26, No. 11, p. 1582, and JP-A-58-188880 has some problems, such as a low yield, the use of 2-methyl-3-butyn-2-chloride (compound (6)) being relatively unstable.

Although the preparing method described in *Synthesis*, 1995, vol. 6, p. 707 gives an improved yield of 89% by using copper catalyst, it has some problems, such as removal of the copper catalyst being heavy metal, and the use of a large amount of potassium iodide that is not necessarily said to be inexpensive in case where potassium iodide is used, and the like. In addition, a problem regarding the stability of 2-methyl-3-butyn-2-chloride remains. Further, there is problems in the aspects of procedure ability and cost, such as the use of 2-methyl-3-butyn-2-chloride in an amount of 2 times molar of 4-nitrophenol (compound (5)).

The preparing method described in *Tetrahedron Lett.*, 1994, vol. 35, p. 6405 is similar to the above-mentioned method, but the yield is 81% at most in case where 2-methyl-3-butyn-2-chloride is used, the use of trifluoroacetate that gives the highest yield (88%) is clearly disadvantageous in the aspect of cost, and DBU used is also expensive. Therefore, this method is not suitable as an industrial preparing method.

Also, the preparing method described in *Synth. Commun*, 1989, vol. 19, p. 1255 is not suitable as an industrial preparing method from viewpoint of low yield (45%) and the cost of expensive DEAD or the like.

The preparing method described in *J. Org. Chem.*, 1972, vol. 37, p. 841 can be said to be a preparing method excellent in the cost and procedure ability as it use 2-methyl-3-butyn-2-ol and 4-nitrofluorobenzene as raw materials that are relatively inexpensive and stable, and it does not use catalysts such as heavy metal. However, this method has problems such as low yield of 35%, long reaction time (room temperature, 3 days) or the like.

DISCLOSURE OF THE INVENTION

In order to dissolve the above-mentioned problems, the present inventors eagerly investigated reaction condition between 4-nitrofluorobenzene and an alkoxide of 2-methyl-3-butyn-2-ol. As a result of it, they found a preparing method, which is excellent in procedure ability and provides intended compounds in a good yield, and they consequently completed the present invention.

That is, the present invention relates to a method for producing an acetylene compound of formula (3)

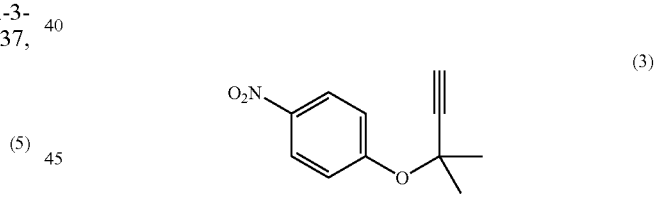

(3)

characterized by reacting 4-nitrofluorobenzene of formula (1)

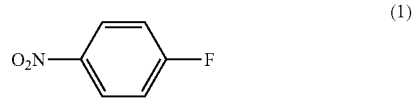

(1)

with an alkoxide of 2-methyl-3-butyn-2-ol of formula (2)

(2)

at −20 to 10° C.

In addition, it is found that the method according to the present invention can inhibit the production of by-product (compound (4)) that cannot be easily removed in the subsequent steps.

(4)

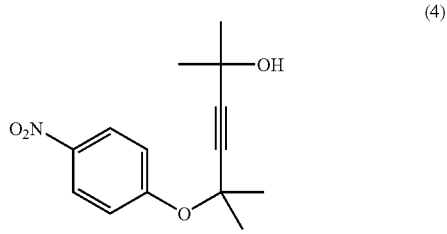

BEST MODE FOR CARRYING OUT THE INVENTION

The process for producing the acetylene compound of formula (3) will be explained.

The acetylene compound of formula (3) can be produced in a good yield by reacting an alkoxide of 2-methyl-3-butyn-2-ol of formula (2) with 4-nitrofluorobenzene of formula (1) in a solvent at −20 to 10° C.

As the alkoxide of 2-methyl-3-butyn-2-ol of formula (2) used in the present invention, metal alkoxides are generally used, and as the metal of the metal alkoxide, alkali metal such as sodium, potassium or lithium or the like is preferable, and sodium is more preferable from viewpoint of ease of handling and reactivity.

The used amount of the alkoxide of 2-methyl-3-butyn-2-ol of formula (2) is 0.5 to 20 times moles based on the used amount of 4-nitrofluorobenzene of formula (1). In the meantime, as the yield is lowered in the used amount of 1 time mole or less, the amount of 1 time mole or more is preferable, and the amount of 1 to 3 times moles is more preferable from viewpoint of cost.

As the procedure process of the reaction, it is preferable to add dropwise 4-nitrofluorobenzene of formula (1) to a solution composed of a solvent and the alkoxide of 2-methyl-3-butyn-2-ol of formula (2).

The time required for the dropwise addition is preferably 0.5 to 5 hours although it is not limited so long as a rapid rise in temperature in the reaction system does not occur and a set temperature is maintained.

The solvents used in the present invention include amide type solvents such as N,N-dimethylacetamide, N,N-dimethylformamide, N-methylpyrrolidone, N,N'-dimethylimidazolidinone or the like, aromatic hydrocarbon type solvents such as toluene, xylene or the like, aliphatic hydrocarbon type solvents such as hexane, heptane or the like, and halogen containing hydrocarbon type solvents such as dichloromethane, chloroform or the like, and mixed solvents of plural solvents mentioned above.

Preferable solvents include amide type solvents, more preferably N,N-dimethylacetamide and N,N'-dimethylimidazilidinone, from viewpoint of the yield of the acetylene compounds of formula (3).

Used amount of the solvent is preferably 2 mass times or more that of 4-nitrofluorobenzene of formula (1), and more preferably, for example 2 to 4 mass times or for example 2 to 3 mass times from viewpoint of cost.

Although the reaction temperature ranges from −20° C. to 10° C., it is preferably a range of −10 to 0° C. from viewpoint of the elongation of reaction time due to lowering of reaction temperature and the inhibition of production of by-product of formula (4).

As the reaction time and reaction temperature cannot be specified in general as they depend on the used amount of the alkoxide or the like.

The acetylene compound of formula (3) being a product can be obtained as a crude product by adding water, then extracting with an organic solvent such as toluene, and washing and then distilling out the solvent.

The crude product can be used as such for the production of a benzopyran intermediate, and it can be purified by column chromatography or distillation, etc., if necessary.

The alkoxide of 2-methyl-3-butyn-2-ol of formula (2) being a raw material in the present invention can be generally produced by processing 2-methyl-3-butyn-2-ol of formula (2) with a metal hydride such as sodium hydride, potassium hydride or the like, or with a metal such as metal sodium, metal potassium, metal lithium, or the like.

The acetylene compound of formula (3) produced according to the present invention is led to a benzopyran derivative that is an intermediate for synthesizing an antifibrillatory agent or a hypotensive agent, by a preparation method shown in the following reaction scheme.

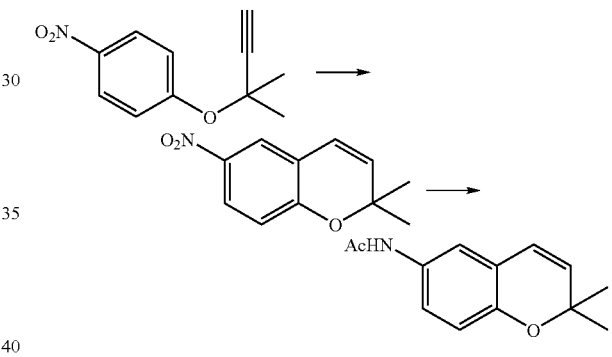

That is, the acetylene compound of formula (3) can be converted to an intermediate for synthesizing the above-mentioned antifibrillatory agent or hypotensive agent, by cyclizing it under heating to lead a benzopyran compound, and reducing and acetylating the resulting compound.

The by-product of formula (4) formed in the production of the acetylene compound of formula (3) cannot be perfectly removed even by crystallization of the above-mentioned acetylamino form. Therefore, it is important for improvement in efficiency of the subsequent preparation to inhibit the formation of the by-product of formula (4) in the production of the acetylene compound of formula (3).

Hereinafter, the present invention is concretely described according to examples to which the present invention is not limited.

In the meantime, HPLC relative area percentage was measured under the following analytical condition:

Column: L-Column ODS φ4.6×250 mm (manufactured by Chemicals Evaluation Research Institute, Japan);

Elution solution:
  0 to 45 min $CH_3CN$-0.01 M $AcONH_4$ (45/55 v/v)
  45 to 65 min $CH_3CN$-0.01 M $AcONH_4$ (45/55 v/v→95/5 v/v)
  65 to 85 min $CH_3CN$-0.01 M $AcONH_4$ (95/5 v/v);

Detection: UV (254 nm);

Flow rate: 1 mL/min.;

Column temperature: 40° C.

EXAMPLE 1

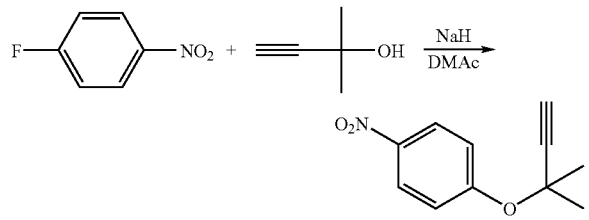

To a 300 mL-reaction flask equipped with a thermometer, a stirrer and a dropping funnel, 96.0 g of N,N-dimethylacetamide (DMAC) and 11.6 g (290 mmol) of 60% sodium hydride (suspension in mineral oil) were added, and 25.2 g (300 mmol) of 2-methyl-3-butyn-2-ol was added dropwise with stirring under cooling with ice to produce an alkoxide (dropwise addition time: 2 hours).

After stirring for 30 minutes, 33.8 g (240 mmol) of 4-nitrofluorobenzene was added dropwise (under cooling with ice, dropwise addition time: 1.5 hour), and after completion of dropwise addition the resulting mixture was stirred at the same temperature for 18 hours. To the reaction mixture, 480 mL of water and 480 mL of toluene were added and the resulting mixture was shaken. After allowing to stand, the mixture was separated into two-phase and the toluene phase was taken out. The aqueous phase was extracted with 240 mL of toluene again and the resulting toluene phase was combined with the toluene phase obtained previously, washed with 240 mL of water, and then the solvent was distilled off to obtain a crude product (63.0 g) of the acetylene compound of formula (3) being a desired product. The crude product was purified with silica gel column chromatography to obtain 44.0 g (yield 90%) of the desired product as yellow oily product.

$^1$H-NMR (CDCl$_3$) ppm: 8.18(2H, d, J=9.2 Hz), 7.30(2H, d, J=9.2 Hz), 2.68(1H, s), 1.73(6H, s)

EXAMPLE 2

To a 2 L-reaction flask equipped with a thermometer, a stirrer and a dropping funnel, 283 g of N,N-dimethylacetamide (DMAc) was added, the resulting mixture was cooled to −13 to −12° C. and 34.3 g (856 mmol) of 60% sodium hydride (suspension in mineral oil) was added thereto. Then, 74.5 g (886 mmol) of 2-methyl-3-butyn-2-ol was added dropwise to produce an alkoxide (internal temperature: −10 to −8° C., dropwise addition time: 3.5 hours).

After stirring for 1.5 hour, 100 g (709 mmol) of 4-nitrofluorobenzene was added dropwise (internal temperature: −10 to −5° C., dropwise addition time: 1.5 hour), and after completion of dropwise addition the resulting mixture was stirred at the same temperature for 38 hours. Under the condition below 10° C., 1420 mL of water was added to the reaction mixture, after stirring for 1 hour, 1420 g of ethyl acetate was added thereto and shaken and the resulting mixture was allowed to stand, separated into two-phase and the ethyl acetate phase was taken out. The aqueous phase was extracted with 709 g of ethyl acetate and the resulting ethyl acetate phase was combined with the ethyl acetate phase obtained previously, washed with 709 g of water, and then the solvent was distilled off to obtain a crude product (177 g) of the acetylene compound of formula (3) being a desired product.

HPLC relative area percentages of acetylene compound of formula (3) and the by-product of formula (4) after reaction for 38 hours and of the crude products are shown in Table 1.

Table 1

|                     | (3)    | (4)   |
|---------------------|--------|-------|
| 38 hours-reaction   | 95.0%  | 0.5%  |
| Crude product of (3)| 93.8%  | 0.5%  |

REFERENTIAL EXAMPLE 1

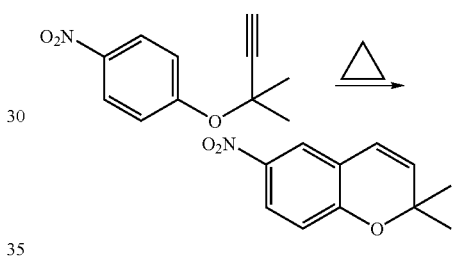

To a 1 L-reaction flask equipped with a thermometer, a stirrer, Dimroth condenser and a dropping funnel, 162 g of o-dichlrobenzene was added, heated to 170° C., and the total amount of the crude product of the acetylene compound of formula (3) obtained in Example 2 dissolved in 186 g of o-dichlorobenzene was added dropwise over 3 hours and 40 minutes thereto (internal temperature: 168 to 176° C.). After completion of dropwise addition the resulting mixture was stirred at the same temperature for 1 hour and the solvent was distilled off to obtain 169 g of a crude product of 2,2-dimethyl-6-nitro-2H-1-benzopyran being a desired product. The crude product was dissolved in a mixed solvent of 317 g of methanol and 56 g of water by heating, and gradually cooled to 2° C., and then was subjected to crystallization for 2 hours and 30 minutes at 0 to 5° C. The resulting crystal was taken by filtration and washed, then dried under a reduced pressure at 50° C. to obtain 137 g (yield: 94%) of 2,2-dimethyl-6-nitro-2H-1-benzopyran. As the crystal was contaminated by mineral oil of sodium hydride and the like, it was subjected to an internal standard determination, and had a purity of 89.4%. Consequently, the yield was 84% in the aggregate of 2 steps. The values of physical property of the sample obtained by purifying with silica gel column chromatography were as follows.

MP: 74.6 to 74.7° C.

$^1$H-NMR (CDCl$_3$) ppm: 8.02(1H, dd, J=8.9, 2.8 Hz), 7.89(1H, d, J=2.8 Hz), 6.81(1H, d, J=8.9 Hz), 6.36 (1H, d, J=9.9 Hz), 5.75 (1H, d, J=9.9 Hz), 1.48 (6H, s)

EXAMPLES 3 to 5

Effect of Reaction Temperature and Amount of Solvent

Except that the reaction temperature and the amount of solvent were altered, the reaction was carried out under the similar condition to that of Example 2. HPLC relative area percentages of acetylene compound of formula (3) and the by-product of formula (4) after the conclusion of the reaction and of the crude products are shown in Table 2.

In the meanwhile, the reaction time was altered depending on the reaction condition.

Further, the amount of solvent was shown in mass times based on the used amount of 4-nitrofluorobenzene of formula (1).

For comparison, the results of Example 2 were also shown.

Table 2

| Example No. | Amount of solvent (mass times) | Temperature (° C.) | Time (hr) | Porportion after reaction (%) (3) | (4) | Proportion of crude products (3) | (4) |
|---|---|---|---|---|---|---|---|
| 2 | 2.83 | −10 to −5 | 38 | 95.0 | 0.5 | 93.8 | 0.5 |
| 3 | 2.84 | −15 to −10 | 90 | 96.8 | 0.3 | 97.1 | 0.3 |
| 4 | 1.85 | −10 to −3 | 41 | 93.2 | 0.8 | 93.1 | 0.8 |
| 5 | 3.85 | −10 to −2 | 17 | 92.8 | 0.7 | 94.2 | 0.5 |

EXAMPLE 6

Example in which N,N'-dimethylimidazolidinone (DMI) was Used as a Solvent

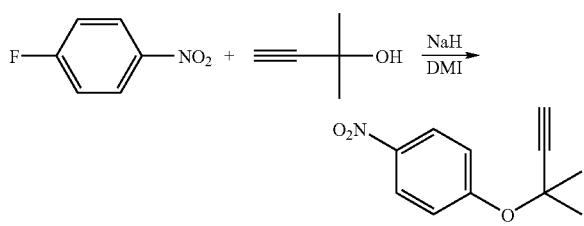

To a 300 mL-reaction flask equipped with a thermometer, a stirrer and a dropping funnel, 96.0 g of N,N'-dimethylimidazolidinone (DMI) and 11.6 g (290 mmol) of 60% sodium hydride (suspension in mineral oil) were added, and 25.2 g (300 mmol) of 2-methyl-3-butyn-2-ol was added dropwise with stirring under cooling with ice to produce an alkoxide (internal temperature: 10° C. or less, dropwise addition time: 1.5 hour, stirring for 30 minute after dropwise addition).

Then, 33.8 g (240 mmol) of 4-nitrofluorobenzene was added dropwise, and the resulting mixture was reacted with stirring for 18 hours under cooling with ice. To the reaction mixture, 480 mL of toluene and 480 mL of water were added and the resulting mixture was shaken. After allowing to stand, the mixture was separated into two-phase and the toluene phase was taken out. The aqueous phase was extracted with 240 mL of toluene and the resulting toluene phase was combined with the toluene phase obtained previously. The combined toluene phase was dried over anhydrous sodium sulfate and filtered, and then the solvent was distilled off to obtain a crude product of the acetylene compound of formula (3) being an desired product. The crude product was subjected to silica gel column chromatography (500 g of silica gel, elution solution: ethyl acetate-hexane=1/20) to obtain 43.5 g (yield 89%) a purified product of the acetylene compound of formula (3) as yellow oily product. HPLC analysis showed that the relative area percentage of the desired product was 91.2% and the relative area percentage of 4-nitrofluorobenzene was 7.9%. As 4-nitrofluorobenzene showed a sensitivity ratio of 4 times, the corrected HPLC purity thereof was 97.9%.

COMPARATIVE EXAMPLE 1

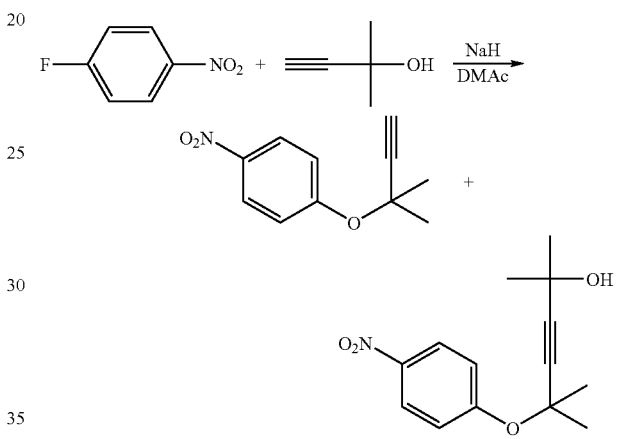

To a 1 L-reaction flask equipped with a thermometer, a stirrer and a dropping funnel, 96 g of N,N-dimethylacetamide (DMAc) was added, the resulting mixture was cooled to 3° C. and 11.6 g (289 mmol) of 60% sodium hydride (suspension in mineral oil) was added thereto. Then, 25.2 g (299 mmol) of 2-methyl-3-butyn-2-ol was added dropwise to produce an alkoxide (internal temperature: 3 to 10° C., dropwise addition time: 1 hour).

Then, 33.8 g (239 mmol) of 4-nitrofluorobenzene was added dropwise (internal temperature: 2 to 5° C., dropwise addition time: 1.5 hour), and after completion of dropwise addition the resulting mixture was stirred at 10 to 15° C. for 20 hours. Thereafter, similarly to the procedure of Example 2, a crude product of the acetylene compound of formula (3) was obtained.

HPLC relative area percentages of acetylene compound of formula (3) and the by-product of formula (4) after reaction for 18 hours and of the crude product are shown in Table 3.

Table 3

|  | (3) | (4) |
|---|---|---|
| 18 hours-reaction | 72.2% | 1.2% |
| Crude product of (3) | 83.1% | 1.5% |

COMPARATIVE EXAMPLE 2

Reaction Between 4-nitrophenol and 2-methyl-3-butyn-2-chloride

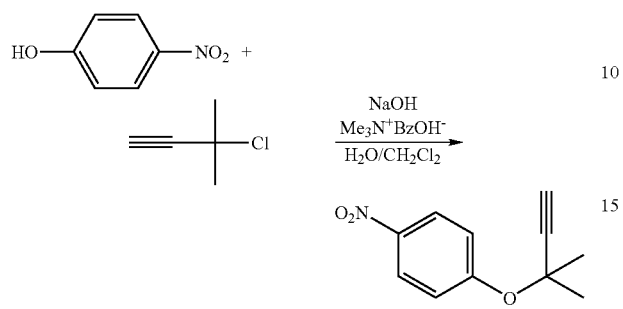

To a 3 L-reaction flask equipped with a thermometer and a stirrer, 148 g (1.06 mol) of nitrophenol and 1000 mL of water were added, sodium hydroxide aqueous solution [NaOH 64.7 g (1.62 mol)/$H_2O$ 100 mL] was added and dissolved thereto (temperature was raised to 35° C. due to exothermic reaction). Then, 1100 mL of dichloromethane, 166 g (1.62 mol) of 2-methyl-3-butyn-2-chloride and 92.0 g of trimethylbenzyl ammonium hydroxide (40% methanol solution) were added successively, and the resulting mixture was stirred at room temperature for 5 days. The stirred solution was allowed to stand, separated into two-phase and the dichloromethane phase was taken out. The aqueous phase was extracted with 500 mL of chloroform and the resulting chloroform phase was combined with the dichloromethane phase obtained previously. The combined phase was washed with 1000 g of 10% sodium hydroxide aqueous solution, 700 mL of water and 500 mL of water, successively, and then dried over anhydrous sodium sulfate. The resulting solution was subjected to filtration and then the solvent distillation to obtain 71.3 g (yield 33%) of the acetylene compound of formula (3) being a desired product as black brown oily product.

The present invention can establish a process for producing the acetylene compound of formula (3) that is useful as an intermediate of pharmaceuticals, from 4-nitrofluorobenzene that is inexpensively available, in industrially and economically advantageous manner.

INDUSTRIAL APPLICABILITY

The acetylene compound of formula (3) produced according to the method of the present invention is useful as for example an intermediate for synthesizing an antifibrillatory agent or a hypotensive agent, and therefore it is beneficial in pharmaceutical industry and the like.

The invention claimed is:

1. A method for producing an acetylene compound of formula (3)

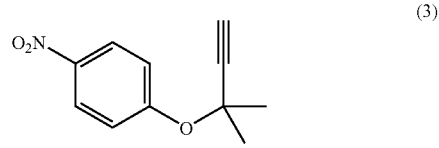

characterized by reacting 4-nitrofluorobenzene of formula (1)

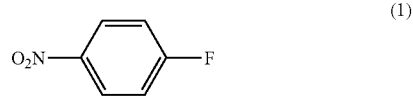

with an alkoxide of 2-methyl-3-butyn-2-ol of formula (2)

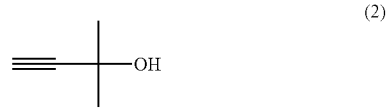

at −20 to 10° C.

2. The method for producing an acetylene compound according to claim 1, wherein an amide type solvent is used as a solvent.

3. The method for producing an acetylene compound according to claim 1, wherein the amount of the solvent used is 2 mass times or more that of 4-nitrofluorobenzene.

4. The method for producing an acetylene compound according to claim 2, wherein the amount of the solvent used is 2 mass times or more that of 4-nitrofluorobenzene.

* * * * *